United States Patent
Fanselow et al.

(10) Patent No.: US 10,371,720 B2
(45) Date of Patent: Aug. 6, 2019

(54) METHOD FOR PRODUCING A SENSOR

(71) Applicant: Endress+Hauser Conducta GmbH+Co. KG, Gerlingen (DE)

(72) Inventors: Christian Fanselow, Geringswalde (DE); André Pfeifer, Schkopau (DE); Thomas Nagel, Dresden (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 15/801,672

(22) Filed: Nov. 2, 2017

(65) Prior Publication Data

US 2018/0128855 A1    May 10, 2018

(30) Foreign Application Priority Data

Nov. 4, 2016 (DE) .......................... 10 2016 121 108

(51) Int. Cl.
| | |
|---|---|
| *G01R 3/00* | (2006.01) |
| *B65B 51/22* | (2006.01) |
| *B29C 65/00* | (2006.01) |
| *G01R 15/14* | (2006.01) |
| *G01N 27/07* | (2006.01) |

(52) U.S. Cl.
CPC .............. *G01R 3/00* (2013.01); *G01N 27/07* (2013.01); *G01R 15/14* (2013.01)

(58) Field of Classification Search
CPC ........... G01R 3/00; G01R 15/14; G01N 27/07
See application file for complete search history.

(56) References Cited

U.S. PATENT DOCUMENTS

| | | | |
|---|---|---|---|
| 6,195,013 B1* | 2/2001 | Robinson | G01F 23/74 116/228 |
| 2009/0250171 A1* | 10/2009 | Wieduwilt | B29C 65/08 156/378 |
| 2010/0232894 A1* | 9/2010 | Burton | B23Q 3/12 408/9 |

(Continued)

FOREIGN PATENT DOCUMENTS

| | | | | |
|---|---|---|---|---|
| DE | 202010016488 U1 * | 2/2011 | | G01D 11/30 |
| DE | 102014111265 A1 | 2/2016 | | |

(Continued)

OTHER PUBLICATIONS

Search Report for German Patent Application No. 10 2016 121 108.7, German Patent Office, dated Jan. 31, 2017, 6 pp.

*Primary Examiner* — Huy Q Phan
*Assistant Examiner* — Zannatul Ferdous
(74) *Attorney, Agent, or Firm* — Mark A. Logan; PatServe

(57) ABSTRACT

The present disclosure relates to a method for producing a sensor comprising the steps of: adapting a sensor adapter of the sensor element to a first section of the process connection, introducing the sensor element with the sensor adapter first into the first section of the process connection, so that the sensor element projects beyond the process connection with a second section and the first section of the process connection and the first section of the sensor element form a gap, connecting the sensor element to the process connection by creating a weld connection between the first section of the process connection and the sensor adapter of the sensor element in the region of the gap.

3 Claims, 2 Drawing Sheets

(56) References Cited

U.S. PATENT DOCUMENTS

| | | | | |
|---|---|---|---|---|
| 2010/0301884 | A1* | 12/2010 | Takane | G01R 1/0735 |
| | | | | 324/762.06 |
| 2013/0008003 | A1* | 1/2013 | Izutani | B23K 9/26 |
| | | | | 29/402.08 |
| 2015/0158247 | A1* | 6/2015 | Heeg | B29C 65/08 |
| | | | | 156/73.1 |
| 2015/0298451 | A1* | 10/2015 | Hutchison | B41C 1/182 |
| | | | | 101/401 |
| 2015/0338363 | A1* | 11/2015 | Dean, Jr. | G01N 27/02 |
| | | | | 73/170.26 |
| 2017/0205815 | A1* | 7/2017 | Wegner | G05B 11/42 |

FOREIGN PATENT DOCUMENTS

| | | |
|---|---|---|
| DE | 102014111266 A1 | 2/2016 |
| DE | 102014117685 A1 | 6/2016 |
| EP | 1516689 A1 | 3/2005 |

* cited by examiner

METHOD FOR PRODUCING A SENSOR

CROSS-REFERENCE TO RELATED APPLICATION

The present application is related to and claims the priority benefit of German Patent Application No. 10 2016 121 108.7, filed on Nov. 4, 2016, the entire contents of which are incorporated herein by reference.

TECHNICAL FIELD

The present disclosure relates to a method for producing a sensor, in particular, a conductivity sensor by means of a process connection and a sensor.

BACKGROUND

Conductivity sensors normally comprise a sensor element that is immersed in the medium to be measured. In order to determine the electrolytic conductivity of the medium, the resistance or conductance of the measuring path in the medium is determined. If the cell constant is known, the conductivity of the measuring medium can then be determined. The sensor element is connected by a line or a cable to a measuring transducer, by means of which the conductivity can be determined using the measured data.

The sensor element, in turn, is connected to a process connection. This combination of the sensor element and process connection will be termed a "sensor" in the following. The process connection serves to connect the sensor to a container in which the medium to be measured is located.

At the connecting site between the sensor element and process connection, corners, edges, burs, and other unevennesses arise from the multi-part construction with seals between the process connection and the sensor element. Dirt, dust, medium, etc., can adhere to these sites. Consequently, such a sensor is unsuitable for hygienic requirements.

German patent application no. DE 102014117685 A1 describes a method for producing a conductivity sensor. The sensor comprises a process connection and a sensor element. The method comprises the following steps.

Initially, a first region of the sensor element is adapted to a first region of the process connection, so that, when the first region of the sensor element is introduced into the first region of the process connection, a second region of the sensor element projects beyond the process connection. Then, both first regions are provided with an adhesive. Subsequently, the first region of the sensor element is introduced into the first region of the process connection, so that the adhesive is arranged in a gap between the first region of the sensor element and the first region of the process connection.

A disadvantage of such a solution is that the adhesive effect of the adhesive attenuates over time.

SUMMARY

The aim of the present disclosure is to present a method for producing a sensor by means of a process connection and sensor element.

The aim is achieved by the subject matter of the present disclosure. The subject matter of the present disclosure is a method for producing a sensor, in particular, a conductivity sensor, by means of a process connection and a sensor element, comprising the steps of:

Adapting a sensor adapter of the sensor element to a first section of the process connection.

Introducing the sensor adapter of the sensor element into the first section of the process connection, so that the sensor element projects beyond the process connection with a sensor tip and the first section of the process connection and the sensor adapter of the sensor element form a gap, and Connecting the sensor element to the process connection by creating a weld connection between the first section of the process connection and the sensor adapter of the sensor element in the region of the gap.

According to an advantageous development, the weld connection is achieved by ultrasonic welding, plastic-bonding joining methods, infrared welding, laser welding, or friction welding.

According to an advantageous variant, the sensor element is connected to the process connection in the region of the gap by ultrasonic welding, wherein the sensor element is placed on an anvil, and the process connection is placed on a sonotrode.

According to an advantageous embodiment, the sensor element is connected to the process connection in the region of the gap by ultrasonic welding, wherein the sensor element is placed on a sonotrode, and the process connection is placed on an anvil.

According to an advantageous embodiment, the weld connection between the process connection and the sensor element is finished by a machining process such as vibratory finishing, carving, deburring, turning, milling, or grinding.

The aim of the present disclosure is also achieved by a sensor in particular, a conductivity sensor that is produced according to at least one of the preceding claims.

BRIEF DESCRIPTION OF THE DRAWINGS

The present disclosure is explained in more detail based upon the following drawings. Illustrated are.

DETAILED DESCRIPTION

The present disclosure will be explained with reference to a conductivity sensor in particular, with reference to a conductive conductivity sensor. The basic concept is, however, applicable to other types of sensors that use metal electrodes. A wide range of sensors are conceivable from the field of process automation, such as pH sensors, amperometric sensors, etc.

Figure 1:
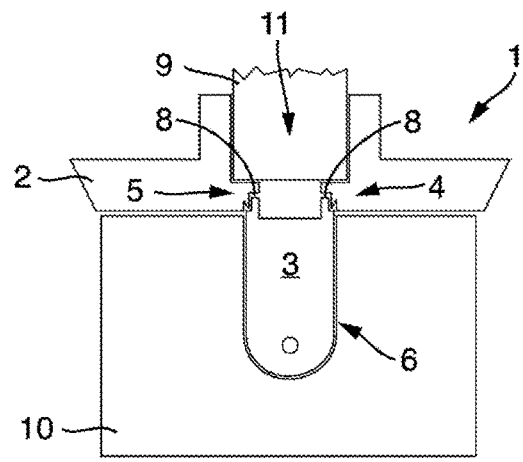
FIG. 1 shows a longitudinal section of a sensor with a sensor element and a process connection, in which the sensor element is arranged on the anvil, and the sonotrode is arranged on the process connection.

FIG. 1 shows a sensor 1 comprising a sensor element 3 and a process connection 2. The sensor element 3 is made of a technical ceramic such as zirconium dioxide in general, of an electrically nonconductive material. In one embodiment, the zirconium dioxide is magnesium-stabilized, aluminum-stabilized, or iridium-stabilized. The process connection 2 is made of a metal in particular, of stainless steel. By means of the process connection 2, the sensor 1 can be attached to a container (not shown).

The sensor element 3 comprises a sensor adapter 4 for introducing the sensor element 3 into the process connection 2, and a sensor tip 6 by means of which the sensor element 3 projects beyond the process connection 2.

An interior of the process connection 2 is divided into two cylindrical sections that each have an inner radius, wherein the second inner radius is greater than the first inner radius. The first section with the smaller outer radius serves to accommodate the sensor adapter 4.

If the sensor element 3 is fastened to the process connection 2, the first inner radius and an outer radius of the sensor adapter 4 form a press fit. In so doing, the second section of the process connection 2 and the sensor adapter 4 of the sensor element 3 form a gap.

The sensor element 3 and the process connection 2 are connected by welding. For this purpose, the gap 8 between the first section 5 of the process connection 2 and the sensor adapter 4 is welded by ultrasonic welding. The ultrasonic welding is accomplished by introducing the sensor element 3 with the sensor tip 6 first into a custom-fit anvil 10. Analogously, a sonotrode 9 is introduced into a custom-fit opening in the process connection such that the gap 8 is arranged between the anvil 10 and the sonotrode. The weld connection is produced by vibrations of the sonotrode.

Figure 2:
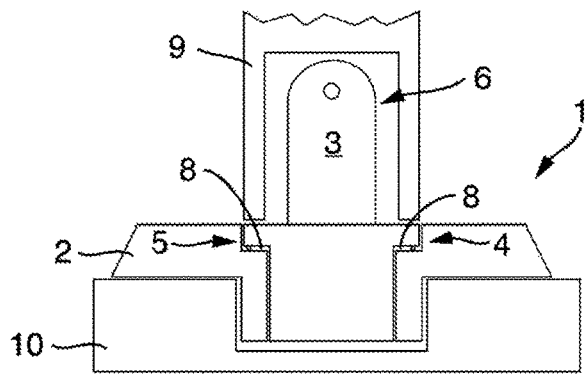
FIG. 2 shows a longitudinal section of a sensor with a sensor element and a process connection, in which the process connection is arranged in the anvil, and the sensor element is arranged within the sonotrode.

FIG. 2 shows a longitudinal section of a sensor 1 with a sensor element 3 and a process connection 2, in which the process connection 2 is arranged in the anvil 10, and the sensor element 3 is arranged within the sonotrode 9. This embodiment shows an alternative sensor production method.

Figure 3:
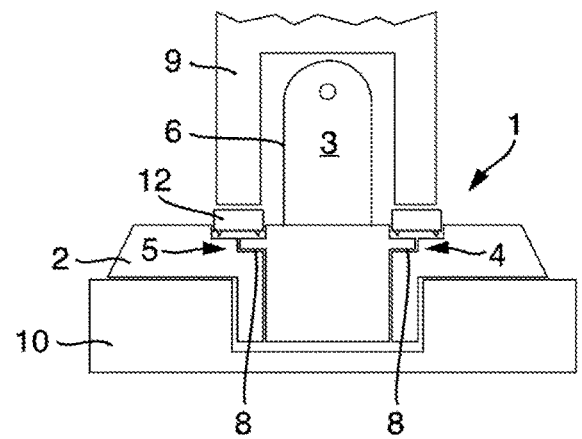
FIG. 3 shows a longitudinal section of a sensor corresponding to FIG. 2, in which the sensor is welded by means of an intermediate ring to the process connection.

FIG. 3 shows a longitudinal section of a sensor 1 corresponding to FIG. 2, in which the sensor 1 is welded by means of an intermediate ring 12 to the process connection 2. If an intermediate ring 12 is used, numerous finishing steps of a contact region between the sensor element 3 and the process connection 2 become superfluous.

Figure 4:
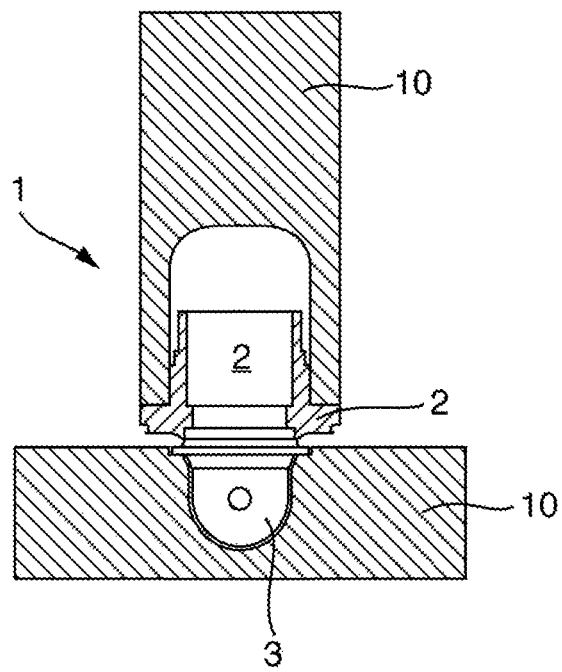
FIG. 4 shows a longitudinal section of a sensor with a sensor element 3 and a process connection 2, in which the process connection is arranged on the sonotrode and the sensor element is arranged on the anvil, and FIG. 5 a sensor that is produced in a manner corresponding to one of the methods described in the description of FIG. 1.

FIG. 4 shows a longitudinal section of a sensor 1 with a sensor element 3 and a process connection 2, in which the process connection 2 is arranged on the sonotrode 9, and the sensor element 3 is arranged on the anvil 10. This embodiment shows an alternative sensor production method.

Figure 5:
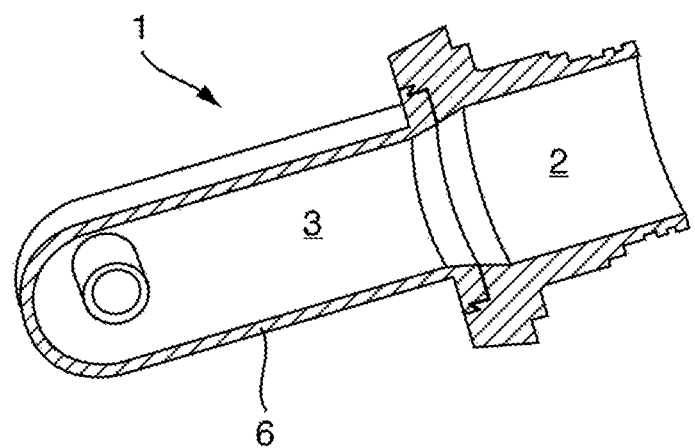

FIG. 5 shows a sensor 1 that is produced in a manner corresponding to one of the methods described in the description of FIG. 1.

The invention claimed is:

1. A method for producing a sensor, comprising:
   adapting a sensor adapter of a sensor element to a first section of a process connection, wherein the process connection includes a custom-fit opening for a sonotrode;
   placing the sensor element with the sensor adaptor on an anvil;
   introducing the sensor element with the sensor adapter into the first section of the process connection such that a sensor tip of the sensor element projects beyond the process connection and the first section of the process connection and the sensor adapter form a gap;
   placing a sonotrode in the custom-fit opening of the process connection such that the gap is between the sonotrode and the anvil; and
   creating an ultrasonic weld connection between the first section of the process connection and the sensor adapter in the region of the gap, thereby connecting the sensor element to the process connection.

2. The method according to claim 1, wherein the sensor is a conductivity sensor.

3. The method according to claim 1, further comprising:
   finishing the weld connection between the process connection and sensor element by a machining process including vibratory finishing, carving, deburring, turning, milling, or grinding.

* * * * *